United States Patent
Kawasaki et al.

(10) Patent No.: US 9,655,498 B2
(45) Date of Patent: May 23, 2017

(54) MEDICAL IMAGE DISPLAYING APPARATUS AND A MEDICAL IMAGE DIAGNOSTIC APPARATUS

(75) Inventors: Tomohiro Kawasaki, Otawara (JP); Nobuyuki Konuma, Utsunomiya (JP)

(73) Assignees: TOSHIBA MEDICAL SYSTEMS CORPORATION, Otawara-shi, Tochigi-ken (JP); KABUSHIKI KAISHA TOSHIBA, Tokyo (JP)

( * ) Notice: Subject to any disclaimer, the term of this patent is extended or adjusted under 35 U.S.C. 154(b) by 552 days.

(21) Appl. No.: 13/993,994

(22) PCT Filed: May 31, 2012

(86) PCT No.: PCT/JP2012/064142
§ 371 (c)(1),
(2), (4) Date: Jun. 13, 2013

(87) PCT Pub. No.: WO2012/165572
PCT Pub. Date: Dec. 6, 2012

(65) Prior Publication Data
US 2014/0081079 A1    Mar. 20, 2014

(30) Foreign Application Priority Data
Jun. 1, 2011   (JP) .................................. 2011-123337

(51) Int. Cl.
*H04N 13/00*   (2006.01)
*A61B 1/00*    (2006.01)
(Continued)

(52) U.S. Cl.
CPC .......... *A61B 1/0005* (2013.01); *A61B 1/0002* (2013.01); *A61B 1/00009* (2013.01);
(Continued)

(58) Field of Classification Search
CPC . A61B 1/0005; A61B 1/00009; A61B 1/0002; A61B 1/00039; A61B 1/041;
(Continued)

(56) References Cited

U.S. PATENT DOCUMENTS 6,590,999 B1 *   7/2003   Comaniciu .............. G06K 9/32
                                                       348/416.1
2005/0251017 A1    11/2005  Azar
(Continued)

FOREIGN PATENT DOCUMENTS

JP   2004-89484 A   3/2004
JP   2006-51332 A   2/2006
(Continued)

OTHER PUBLICATIONS

Nakada, Yuichi et al., "Colonic polyp detection method from 3D abdominal CT images based on local intensity structure analysis", IEIC (Institute of Electronics, Information and Communication Engineers) Technical Report, Aug. 2006, p. 47-52, vol. 106, No. 226, Japan. See English Abstract on p. 47.
(Continued)

*Primary Examiner* — Tat Chio
(74) *Attorney, Agent, or Firm* — Kenichiro Yoshida

(57) ABSTRACT

A medical image displaying apparatus is provided that improves the workability of making a definitive diagnosis in capsule endoscopy. A medical image displaying apparatus of an embodiment is capable of displaying a virtual endoscopic image in a tube based on a viewpoint set inside the tube of the tubular body by using a three-dimensional image of the tubular body, and comprises a capsule endoscopic image storage and a display controller, and the capsule endoscopic image storage stores capsule endoscopic images acquired by a capsule endoscope passing inside the tube. The display
(Continued)

controller displays the capsule endoscopic images based on the location of the viewpoint.

11 Claims, 14 Drawing Sheets

(51) Int. Cl.
| | |
|---|---|
| *A61B 1/04* | (2006.01) |
| *A61B 1/31* | (2006.01) |
| *A61B 6/00* | (2006.01) |
| *G06T 7/00* | (2017.01) |
| *G06T 7/38* | (2017.01) |
| *A61B 6/03* | (2006.01) |

(52) U.S. Cl.
CPC .......... *A61B 1/00039* (2013.01); *A61B 1/041* (2013.01); *A61B 1/31* (2013.01); *A61B 6/032* (2013.01); *A61B 6/463* (2013.01); *A61B 6/5247* (2013.01); *G06T 7/0012* (2013.01); *G06T 7/38* (2017.01); *A61B 1/00016* (2013.01); *A61B 6/03* (2013.01); *A61B 6/5217* (2013.01); *G06T 2207/10068* (2013.01); *G06T 2207/10072* (2013.01); *G06T 2207/30028* (2013.01); *G06T 2207/30032* (2013.01); *G06T 2207/30172* (2013.01); *G06T 2207/30244* (2013.01)

(58) Field of Classification Search
CPC ........... A61B 1/31; A61B 6/032; A61B 6/463; A61B 6/5247; G06T 7/38; G06T 7/0012
See application file for complete search history.

(56) References Cited

U.S. PATENT DOCUMENTS

| | | | | |
|---|---|---|---|---|
| 2008/0312501 | A1* | 12/2008 | Hasegawa | A61B 1/00016 600/117 |
| 2009/0292171 | A1* | 11/2009 | Ito | A61B 1/00009 600/111 |
| 2009/0292175 | A1* | 11/2009 | Akimoto | A61B 1/2676 600/156 |
| 2010/0010304 | A1* | 1/2010 | Kawano | A61B 1/00039 600/117 |
| 2011/0075901 | A1* | 3/2011 | Nakamura | G06F 19/321 382/128 |
| 2011/0245660 | A1* | 10/2011 | Miyamoto | A61B 6/032 600/424 |
| 2012/0033866 | A1 | 2/2012 | Masumoto et al. | |

FOREIGN PATENT DOCUMENTS

| | | |
|---|---|---|
| JP | 2006-61274 A | 3/2006 |
| JP | 2006-230906 A | 9/2006 |
| JP | 2010-46525 A | 3/2010 |
| JP | 2010-264232 A | 11/2010 |
| JP | 2011-173 A | 1/2011 |
| JP | 2011-36600 A | 2/2011 |
| JP | 2011-50590 A | 3/2011 |
| JP | 2011-92681 A | 5/2011 |

OTHER PUBLICATIONS

Hirano, Yasushi and Toriwaki, Jun-Ichiro, "Methods for Structural Analysis of Digital Figures Using Distance Transformation, Medical Imaging Technology," Jan. 2002, p. 13-22, vol. 20 No. 1. See English Abstract On p. 13.

International Search Report Mailed on Jul. 10, 2012 for Corresponding International Application No. PCT/JP2012/064142.

* cited by examiner

MEDICAL IMAGE DISPLAYING APPARATUS AND A MEDICAL IMAGE DIAGNOSTIC APPARATUS

TECHNICAL FIELD

An embodiment of the present invention relates to a medical image displaying apparatus and a medical image diagnostic apparatus.

BACKGROUND

A three dimensional image is acquired using respective modalities of an X-ray computed tomography apparatus (hereinafter, referred to as CT (Computed Tomography)), a magnetic resonance imaging apparatus (hereinafter, referred to as MRI (Magnetic Resonance Imaging)), an X-ray diagnostic apparatus, and an ultrasonic diagnostic apparatus. For example, by means of three-dimensional image processing using perspective representation based on a three-dimensional image acquired by CT, a virtual endoscopic image (VE: Virtual Endoscopy) with viewpoints inside tubular bodies such as a digestive tract, tracheae, blood vessels, etc., may be made (for example, Patent Document 1). It should be noted that a modality may be referred to as a medical image diagnostic apparatus. Moreover, a virtual endoscopic image may be referred to as a CT endoscopic image.

Moreover, by using a capsule endoscope passing inside a tubular body such as a digestive tract, tracheae, blood vessels, etc., capsule endoscopic images from viewpoints inside the tube is acquired.

Regarding virtual endoscopic images and capsule endoscopic images, particularly, a three-dimensional medical image processing/displaying apparatus (multi-modality work station) is used for image diagnosis by displaying lesions such as polyps etc. inside gastrointestinal organs such as the large intestine. It should be noted that the three-dimensional medical image processing/displaying apparatus may simply be referred to as a medical image displaying apparatus.

Examination methods of a digestive tract include large intestine analysis (CT colonography) and small intestine analysis (CT Enterography) upon CT, endoscopy, capsule endoscopy, etc.

In large intestine analysis and small intestine analysis upon CT, polyp lesion candidates are examined using virtual endoscopic images. These are not images actually taken inside the digestive tract; therefore, they are not suitable for definitive diagnosis due to reasons such as the inability to observe the actual color of the inner wall, etc.

In endoscopy, an endoscope is directly inserted inside the digestive tract of the patient, and diagnosis of polyp lesions is carried out from images of the inside of the digestive tract taken by a camera at the tip of the endoscope. Although this allows for definitive diagnosis, there is a weak point due to high invasiveness.

In capsule endoscopy, diagnosis of polyp lesions is carried out from images (capsule endoscopic images) inside the digestive tract repeatedly taken when a small (external diameter: approximately 11 mm, length: approximately 26 mm) capsule-shaped endoscope swallowed by the patient passes inside the digestive tract. This is attracting attention as an examination for definitive diagnosis replacing conventional endoscopes due to its low invasiveness.

Low invasive examinations are required with capsule endoscope, so it is thought that a diagnostic workflow for carrying out definitive diagnosis by capsule endoscopy will become mainstream in the future regarding patients in which the lesion candidates have been determined by digestive tract analysis upon CT.

ABSTRACT OF THE INVENTION

Problems to be Solved by the Invention

However, when a definitive diagnosis is made by capsule endoscopy based on polyp lesion candidates determined during large intestine analysis and/or small intestine analysis upon CT, there is a problem of the workability declining. The following two factors are suggested.

First, virtual endoscopic examination and capsule endoscopy are both carried out independently; therefore, the virtual endoscopic images and the capsule endoscopic images are not associated with each other, making it difficult to select the capsule endoscopic images displaying the lesion candidates.

Secondly, in capsule endoscopy, a capsule endoscope advances inside the digestive tract according to peristaltic movements of the digestive tract, and imaging is carried out as the capsule turns in diverse directions; therefore, a large number of (for example, approximately 60,000) capsule endoscopic images facing diverse directions are obtained. Accordingly, a considerable amount of effort is required to select capsule endoscopic images with the lesion candidates displayed among the large number of images.

This embodiment solves the problems mentioned above, and the purpose thereof is to provide a medical image displaying apparatus and medical image diagnostic apparatus that are capable of improving the workability of definitive diagnosis in capsule endoscopy.

Means for Solving the Problems

In order to solve the problems mentioned above, a medical image displaying apparatus of an embodiment is capable of displaying a virtual endoscopic image in a tube based on a viewpoint set inside the tube of the tubular body by using a three-dimensional image of the tubular body, and comprises a capsule endoscopic image storage and a display controller, and the capsule endoscopic image storage stores capsule endoscopic images acquired by a capsule endoscope passing inside the tube. The display controller displays the capsule endoscopic images based on the location of the viewpoint.

MODES FOR CARRYING OUT THE INVENTION

Next, embodiments of the medical image displaying apparatus are described with reference to respective diagrams.

First Embodiment

Figure 1:
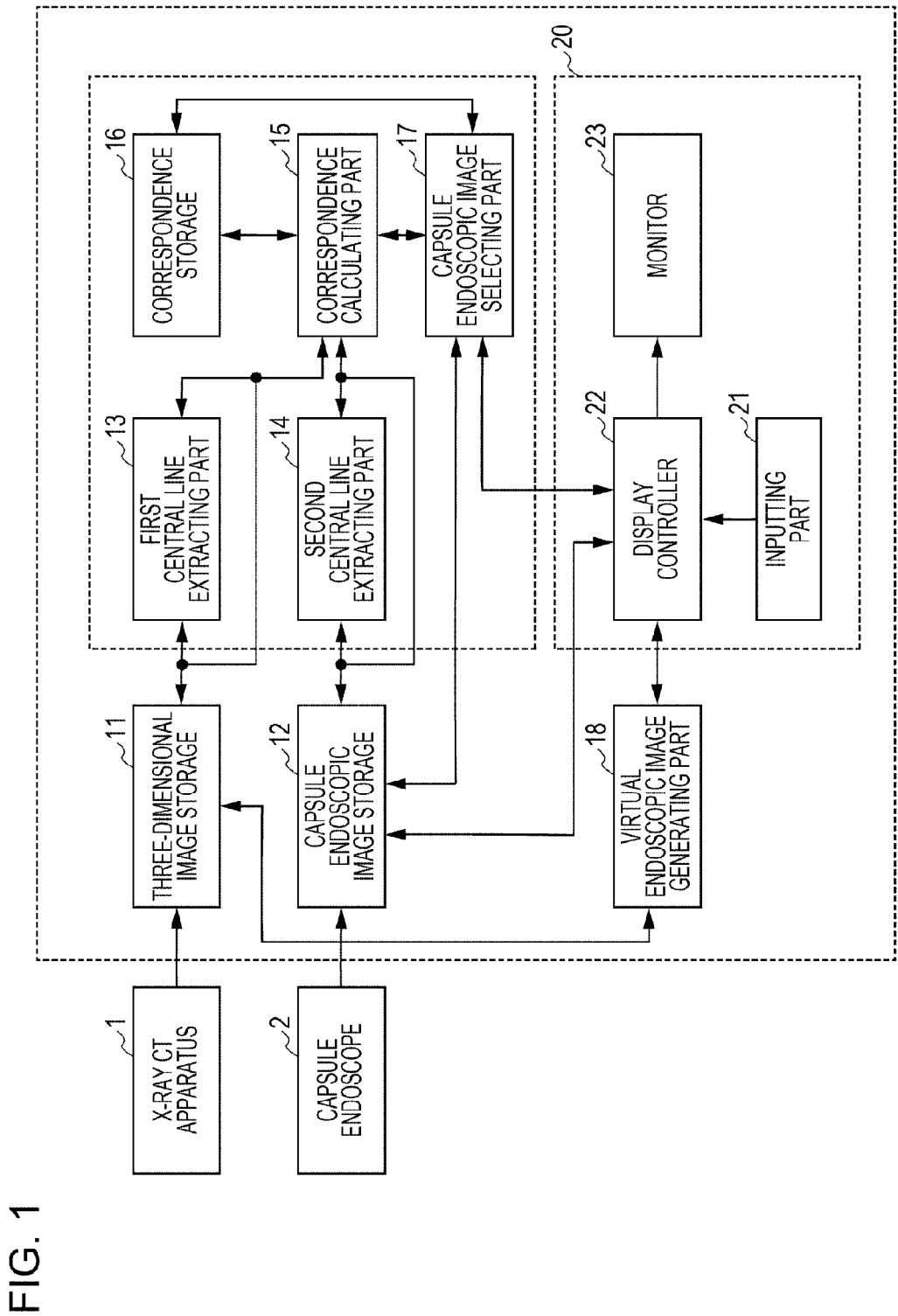
FIG. 1 is a block diagram showing an example of the configuration of the medical image displaying apparatus related to the first embodiment.

A medical image displaying apparatus related to the first embodiment is described with reference to FIGS. 1 to 7, and FIG. 9. FIG. 1 is a block diagram showing an example of the configuration of the medical image displaying apparatus.
(CT)

As shown in FIG. 1, a CT 1 is used as an example of a modality. Three-dimensional images of a tubular body are acquired by the CT 1.

The modality including the CT 1 is connected to PACS (medical image management system), which is a system that may transfer and display digital images as necessary via a network specified by DICOM (Digital Imaging and Communications in Medicine). The three-dimensional images of the tubular body acquired by the modality are transferred to PACS via the network. Furthermore, the three-dimensional images of the tubular body may be stored in a storage (illustration omitted) of the modality.
(Capsule Endoscope)

A capsule endoscope 2 comprises a capsule endoscope, an antenna, and a storage. The capsule endoscope is equipped with an image sensor in order to take images inside the tube of the tubular body. The antenna receives radio waves from the capsule endoscope. The storage stores image data received by the antenna.

The capsule endoscopic images inside the tube are taken by the capsule endoscope moving inside the tube of the tubular body. In the image taking, the locations (three-dimensional locations) and the directions are detected by a location sensor (illustration omitted). The capsule endoscope successively takes images inside the tube of the tubular body at the rate of two images per second. The capsule endoscopic images (image group) obtained by imaging together with the location, direction, and imaging time of the capsule endoscope are stored in the storage of the capsule endoscope 2. The image group is stored in the capsule endoscopic image storage 12.

[Medical Image Displaying Apparatus]

Next, the medical image displaying apparatus is described with reference to FIG. 1.

The medical image displaying apparatus may, for example, use a general computer device as a standard hardware.

As shown in FIG. 1, examples of the medical image displaying apparatus include a three-dimensional image storage 11, a capsule endoscopic image storage 12, a first central line extracting part 13, a second central line extracting part 14, a correspondence calculating part 15, a correspondence storage 16, a capsule endoscopic image selecting part 17, a virtual endoscopic image generating part 18, and a GUI (graphical user interface) 20.

The configurations may be realized by causing a microprocessor equipped in the computer device to carry out an image processing program. Moreover, an image displaying and processing program may be installed in the computer device in advance. Furthermore, the image displaying and processing program may be stored in a storage medium (magnetic disc, magneto-optical disk, optical disk, semiconductor memory, etc.), which may be appropriately installed in the computer device. Furthermore, the image displaying and processing program may be distributed via a network and appropriately installed in the computer device.

It should be noted that regarding the configurations, a part or all may be realized by hardware such as a logic circuit, etc., or may be realized by combining hardware and software.
(Three-Dimensional Image Storage)

The three-dimensional image storage 11 stores three-dimensional images of the tubular body acquired by the CT 1. It should be noted that the three-dimensional image storage 11 may be configured as PACS, may be configured as a storage of the CT 1, or may be independently configured from these.
(Capsule Endoscopic Image Storage)

The capsule endoscopic image storage 12 stores capsule endoscopic images of the tubular body acquired by the capsule endoscope 2. It should be noted that the capsule endoscopic image storage 12 may be configured as PACS, may be configured as a storage of the capsule endoscope 2, or may be independently configured from these.
(First Central Line Extracting Part)

Figure 2A:
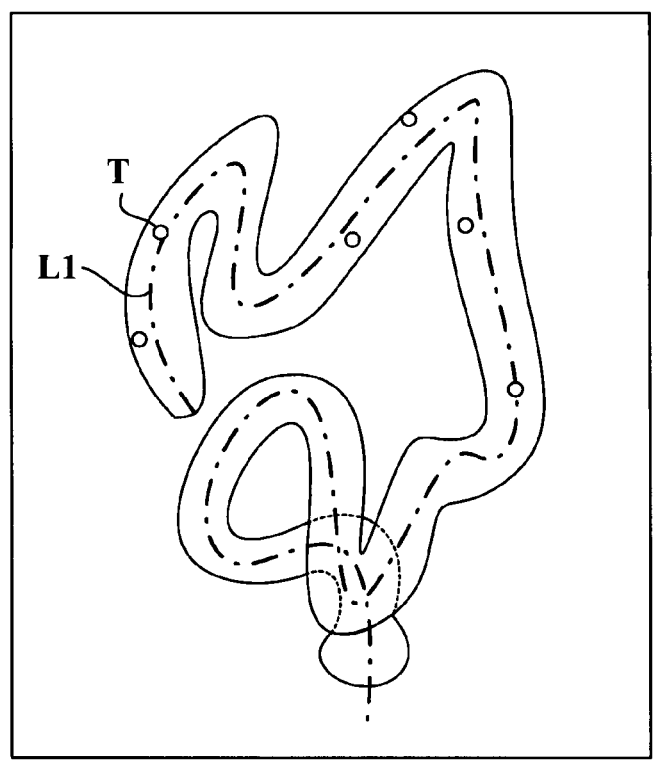
FIG. 2A is an explanatory drawing when extracting a first central line and a lesion candidate.
Figure 2B:
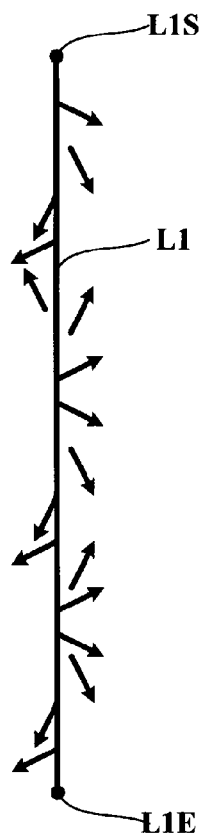
FIG. 2B is an explanatory drawing when extracting a first central line and a lesion candidate.

Next, the first central line extracting part 13 is described with reference to FIG. 2A and FIG. 2B. FIG. 2A and FIG. 2B are explanatory drawings when extracting a first central line and a lesion candidate. FIG. 2A shows a first central line L1 and a lesion candidate T of a large intestine which is an example of the tubular body. FIG. 2B schematically shows the first central line L1 of the large intestine with a straight line and a starting point L1S as well as an end point L1E of the first central line L1. The arrows arranged along the first central line L1 correspond to the directions of the line of sight.

The first central line extracting part 13 automatically extracts the first central line (three-dimensional central line) and a single or a plurality of lesion candidate location(s) of the tubular body based on the three-dimensional images stored in the three-dimensional image storage 11. It should be noted that extraction of the first central line L1 may be determined by the operator using the GUI 20.

The following technique may be used as a specific example of automatic extraction of a three-dimensional central line.

That is, the size of a subject image is expressed in pixels of L lines, M rows, and N columns, distance transformation is carried out on each image, thereby extracting a liner image (for example, Methods for Structural Analysis of Digital Figures Using Distance Transformation, Med Imag Tech Vol. 1, 13-22, January 2002).

As a specific example of automatically extracting the lesion candidate location, focusing on the fact that a colon polyp has a massive intensity structure, the colon polyp is detected using a massive structure emphasizing filter that utilizes eigenvalues of Hessian matrices (for example, Colonic polyp detection method from 3D abdominal CT images based on local intensity structure analysis, The Journal of the Institute of Electronics, Information, and Communication Engineers MI, medical image 106 (226), 47-52, 2006-08-26).

The extracted first central line is stored in the three-dimensional image storage 11 as point-sequence data of the same three-dimensional coordinate space as the three-dimensional image. In the same manner, the extracted lesion candidate location is stored in the three-dimensional image storage 11 as the point coordinate of the same three-dimensional coordinate space as the three-dimensional image.

(Second Central Line Extracting Part)

Figure 3:
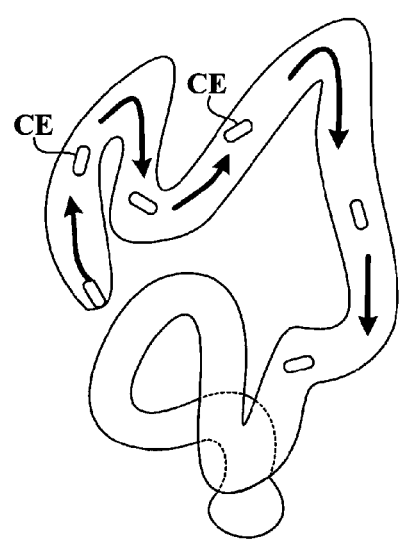
FIG. 3 is an explanatory drawing of the imaging by capsule endoscope.

Next, the second central line extracting part 14 is described with reference to FIG. 3, FIG. 4A, and FIG. 4B. FIG. 3 is an explanatory drawing of the imaging by a capsule endoscope. FIG. 3 shows a capsule endoscope CE that moves inside the large intestine cavity, which is an example of a tubular body.

As shown in FIG. 3, the capsule endoscope takes images (capsule endoscopic images) inside the tube by moving inside the tube of the tubular body. The capsule endoscopic image is accompanied by the location (three-dimensional location) as well as the direction of the capsule endoscope at the time of imaging, and is stored in the capsule endoscopic image storage 12.

Figure 4A:
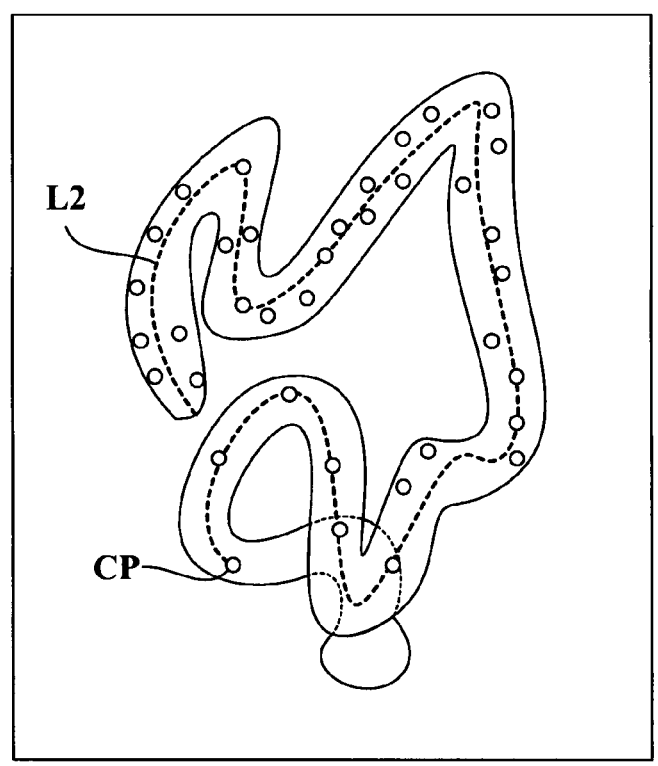
FIG. 4A is an explanatory drawing when extracting a second central line.
Figure 4B:
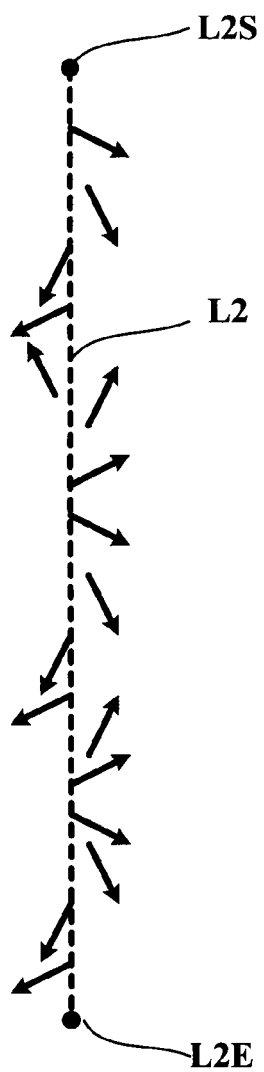
FIG. 4B is an explanatory drawing when extracting a second central line.

FIG. 4A and FIG. 4B are explanatory drawings when extracting the second central line. FIG. 4A shows the location of the capsule endoscope CP and the second central line L2. In FIG. 4B, the transition course (second central line L2) of the capsule endoscope is schematically shown by a straight dotted line, and further the movement starting location (starting point) of the capsule endoscope is denoted by L2S as well as the movement end location (ending point) is denoted by L2E, and furthermore, the direction of the capsule endoscope at each point is shown by an arrow.

As shown in FIG. 4A and FIG. 4B, the second central line extracting part 14 extracts the second central line (three-dimensional central line) based on the location of the capsule endoscopic images.

As a specific extracting method of the second central line, point-sequence data that is obtained by sequentially connecting the coordinates of the three-dimensional locations accompanying the capsule endoscopic image, and by three-dimensionally smoothing the location information of this point-sequence data, the point-sequence data of the second central line is obtained.

(Correspondence Calculating Part)

Figure 5:
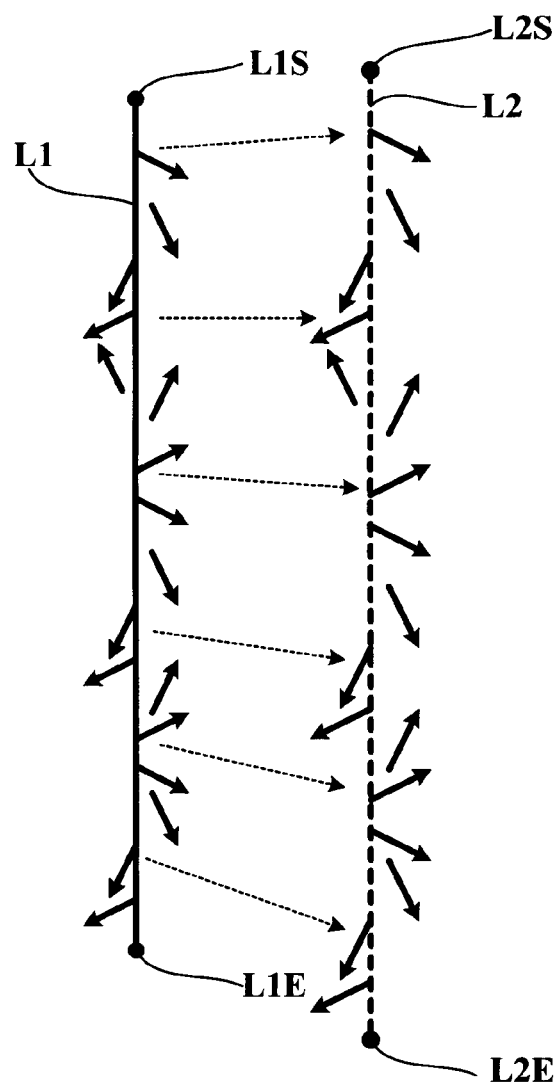
FIG. 5 is an explanatory drawing when obtaining a correspondence of the central lines.

Next, the correspondence calculating part 15 is explained with reference to FIG. 5. FIG. 5 is an explanatory drawing when obtaining the correspondence of the central lines. In FIG. 5, the first central line L1 is indicated with a solid line, while the second central line L2 is indicated with a dotted line. The second central line L2 shown is longer than the first central line L1 because it is not always the case in which the capsule endoscope moves along the central line of the tubular body due to meandering, etc. it should be noted that, in FIG. 5, the arrows arranged along the first central line L1 corresponds to the directions of the line of sight when the virtual endoscopic image is created.

The correspondence calculating part 15 obtains the correspondence between the first central line extracted by the first central line extracting part 13 and the second central line extracted by the second central line extracting part 14 (refer to FIG. 5).

Specifically, correspondence of the locations on the first central line and the locations on the second central line is obtained by a non-linear position adjusting process of the first central line and the second central line. It should be noted that the locations on the first central line correspond to the locations of the viewpoints in the virtual endoscopic images, and the locations on the second central line correspond to the locations of the capsule endoscope.

As a specific method of the non-linear position adjusting process, the correspondence between points on the first central line and the second central line is determined such that the degree of similarity of the tangent vectors at each point on the first central line and the second central line becomes the greatest. That is, as schematically shown in FIG. 2B, the tangent vector of the central line is obtained for each point from the starting point L1S to the end point L1E of the first central line, and in the same manner, as schematically shown in FIG. 4B, the tangent vector of the central line is obtained for each point from the starting point L2S to the end point L2E of the second central line. Subsequently, a correspondence of the points of the first central line and the second central line is obtained such that the total sum of the inner products of arbitrary points of the first central line and arbitrary points of the second central line becomes the greatest.

(Correspondence Storage)

The correspondence storage 16 stores the obtained correspondence between the first central line and the second central line. As an example of the correspondence storage 16, there is a table in which each point on the first central line and each point on the second central line are associated and stored. It should be noted that, without limitation to this, the correspondence storage 16 may be a mathematical expression of a correspondence in order to obtain a point of the second central line based on each point of the first central line.

(Capsule Endoscopic Image Selecting Part)

Figure 6:
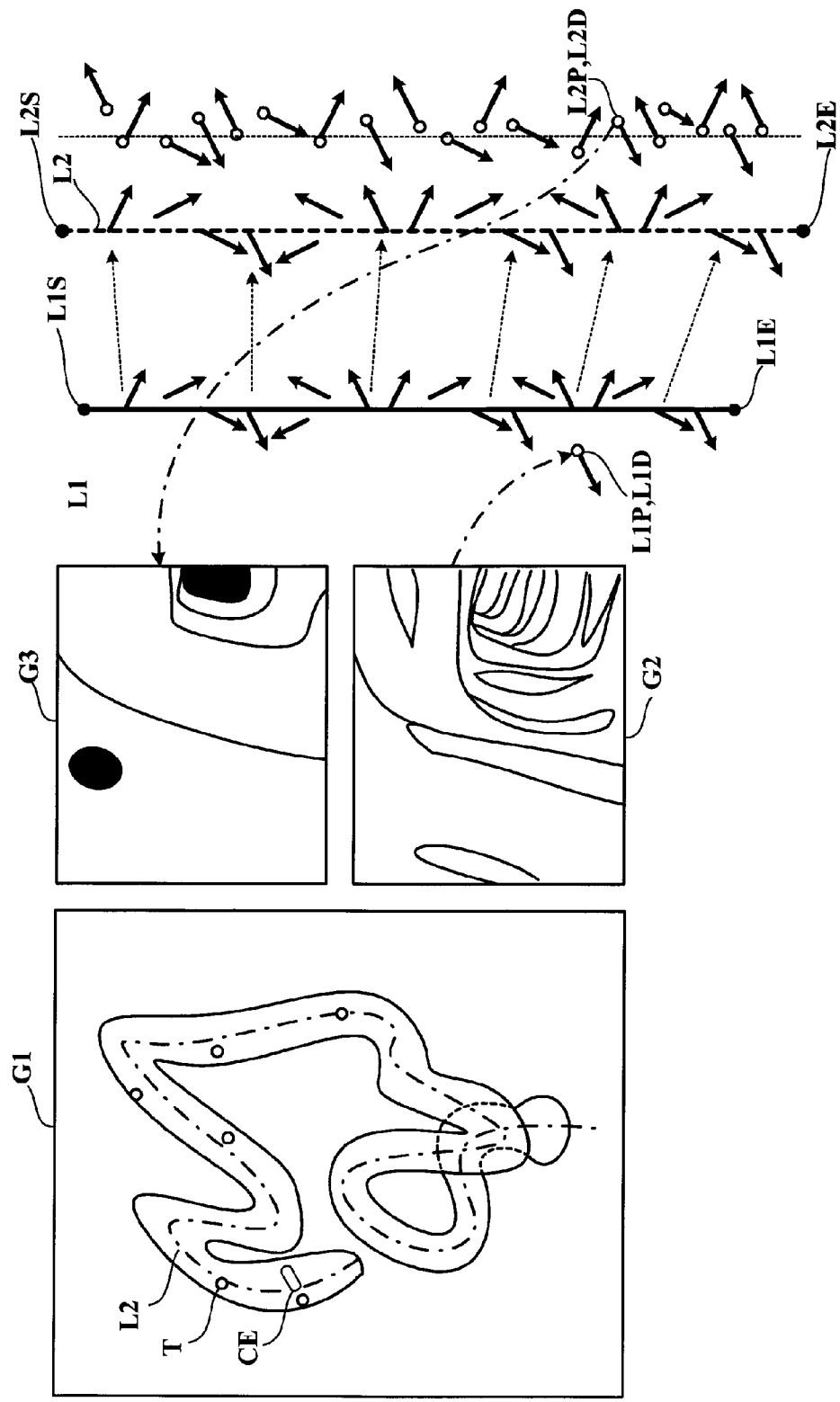
FIG. 6 is an explanatory drawing when the capsule endoscopic image is selected.

Next, the capsule endoscopic image selecting part 17 is described with reference to FIG. 6. FIG. 6 is an explanatory drawing when selecting the capsule endoscopic image.

Based on the correspondence stored in the correspondence storage 16, the capsule endoscopic image selecting part 17 selects the capsule endoscopic image of the closest location and direction to the location and direction for displaying the virtual endoscopic image from among the capsule endoscopic images stored in the capsule endoscopic image storage 12. It should be noted that the direction of the first central line corresponds to the direction of the line of sight of the virtual endoscopic image. Moreover, the direction of the second central line corresponds to the direction of the line of sight of the capsule endoscope.

Specifically, the capsule endoscopic image selecting part 17 receives input of a location on the first central line from the GUI 20, and obtains the location on the second central line corresponding to this location based on the correspondence stored in the correspondence storage 16. Furthermore, the capsule endoscopic image selecting part 17 extracts the image group taken near the location on the second central line from among the capsule endoscopic images stored in the capsule endoscopic image storage 12. Furthermore, the capsule endoscopic image selecting part 17 obtains the direction on the second central line relatively closest to the direction on the first central line from the image groups, and furthermore, obtains the location on the second central line corresponding to the direction on the second central line. Furthermore, the capsule endoscopic image selecting part 17 selects the capsule endoscopic image associated with the obtained location and direction on the second central line from among the capsule endoscopic images stored in the capsule endoscopic image storage 12. The selected capsule endoscopic image is determined to be the capsule endoscopic image closest to the virtual endoscopic image made based on the location and direction on the first central line.

(Virtual Endoscopic Image Generating Part)

The virtual endoscopic image generating part 18 receives the location and direction on the first central line from the GUI 20, and generates, using the three-dimensional images read from the three-dimensional image storage 11, the virtual endoscopic image by a three-dimensional image processing using a perspective representation based on the location and direction on the first central line.

(GUI)

The GUI 20 comprises an inputting part 21, a display controller 22, and a monitor 23.

An example of the inputting part 21 includes a keyboard, pointing devices such as a mouse, joystick, etc.

The display controller 22 displays a three-dimensional image, a virtual endoscopic image (including its first central line), a capsule endoscopic image, etc. on the monitor 23, and also outputs the location on the first central line corresponding to the display region indicated by the inputting part 21 to the capsule endoscopic image selecting part 17. It should be noted that the initial location and the initial direction on the first central line are stored in the internal memory (illustration omitted) of the GUI 20 in advance.

[Actions of Medical Image Displaying Apparatus]

Figure 8:
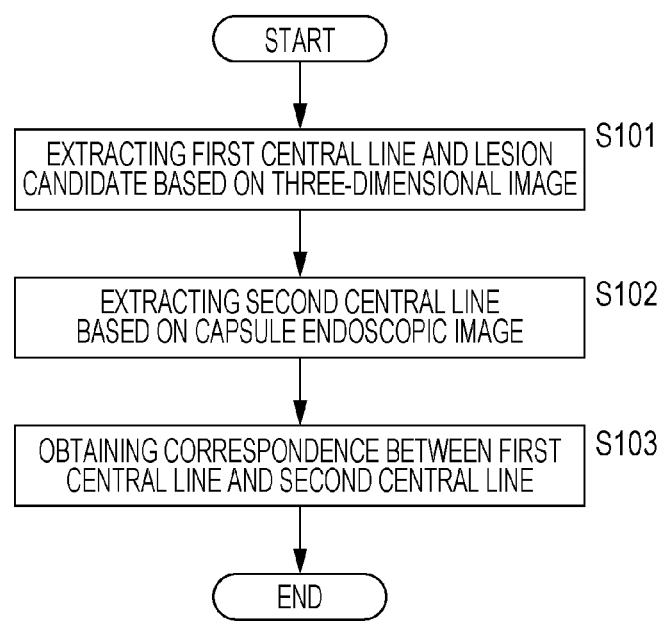
FIG. 8 is a flow chart showing the series of actions in obtaining a correspondence between the first central line and the second central line.
Figure 9:
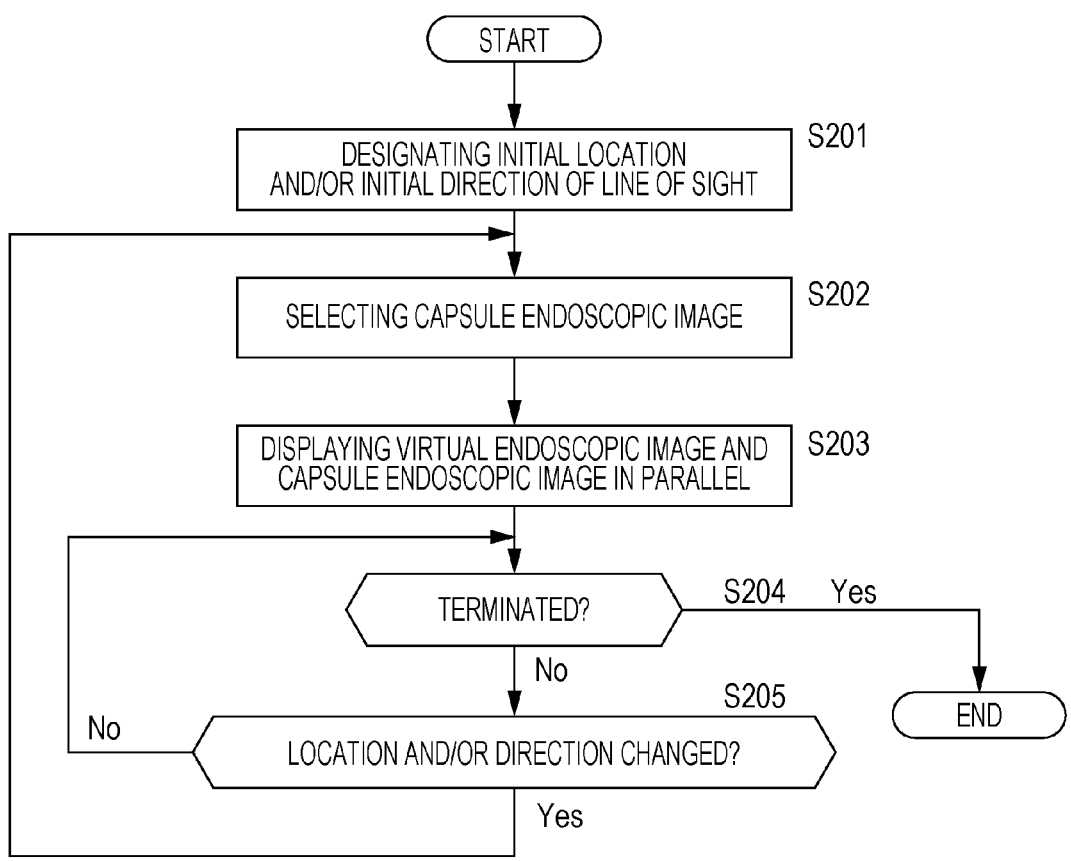
FIG. 9 is a flow chart showing the series of actions in selecting a capsule endoscopic image displaying the lesion candidate.

Next, a series of actions of the medical image displaying apparatus are described with reference to FIG. 8 and FIG. 9. FIG. 8 is a flow chart showing the series of actions in obtaining a correspondence between the first central line and the second central line.

(S101)

As shown in FIG. 8, in S101, the first central line extracting part 13 extracts the first central line and the lesion candidate location based on the three-dimensional image read from the three-dimensional image storage 11 (refer to FIG. 2).

The extracted first central line (point-sequence data) and the lesion candidate location are stored in the three-dimensional image storage 11.

(S102)

In S102, the second central line extracting part 14 extracts the second central line (point-sequence data) passed by the capsule endoscope based on the location (three-dimensional location) of the capsule endoscope stored in the capsule endoscopic image storage 12.

(S103)

In S103, the correspondence calculating part 15 obtains a correspondence between the location of the first central line obtained in S101 and the location of the second central line obtained in S102. The obtained correspondence is stored in the correspondence storage 16.

The correspondence between the first central line and the second central line as mentioned above is obtained in advance. For example, a definitive diagnosis is carried out in capsule endoscopy based on the lesion candidate examined during large intestine analysis and/or small intestine analysis upon the CT 1 using the correspondence. It should be noted that the correspondence may be obtained when carrying out definitive diagnosis in capsule endoscopy.

Next, the series of actions in carrying out the definitive diagnosis in capsule endoscopy using the correspondence is described with reference to FIG. 9. FIG. 9 is a flow chart showing the series of actions in selecting the capsule endoscopic image in which the lesion candidate is displayed.

(S201: Reading Out the Initial Location, Etc., on the First Central Line)

The initial location and initial direction on the first central line is stored in the internal memory of the GUI 20. As shown in FIG. 9, in S201, the capsule endoscopic image selecting part 17 receives an instruction to start displaying the virtual endoscopic images and the capsule endoscopic images on the monitor 23, and reads the initial location and initial direction on the first central line from the internal memory of the GUI 20.

(S202: Selecting the Capsule Endoscopic Image)

In S202, the capsule endoscopic image selecting part 17 obtains, based on the table stored in the correspondence storage 16, the location on the second central line corresponding to the location on the first central line based on the initial location on the read first central line.

Next, the capsule endoscopic image selecting part 17 extracts the image group taken near the location on the second central line from among the capsule endoscopic images stored in the capsule endoscopic image storage 12.

Next, the capsule endoscopic image selecting part 17 selects the image taken in the direction on the second central line closest to the initial direction on the first central line stored in the GUI 20 in advance among the image groups. The selected image is determined as the capsule endoscopic image closest to the initial location and the initial direction on the first central line.

(S203: Image Display)

In S203, the virtual endoscopic image generating part 18 generates the virtual endoscopic image using the three-dimensional image stored in the three-dimensional image storage 11 based on the initial location and the initial direction on the first central line that are set in the GUI 20 in advance.

The display controller 22 displays, in an interlocking fashion, the capsule endoscopic image obtained in S202 and the virtual endoscopic image generated in S203 on the monitor 23 based on the initial location and the initial direction on the first central line.

Here, regarding two images having a correspondence with each other based on the location and the direction on the central line, interlocking display refers to associating and displaying the two images based on the location and/or the direction of the central line.

Figure 7:
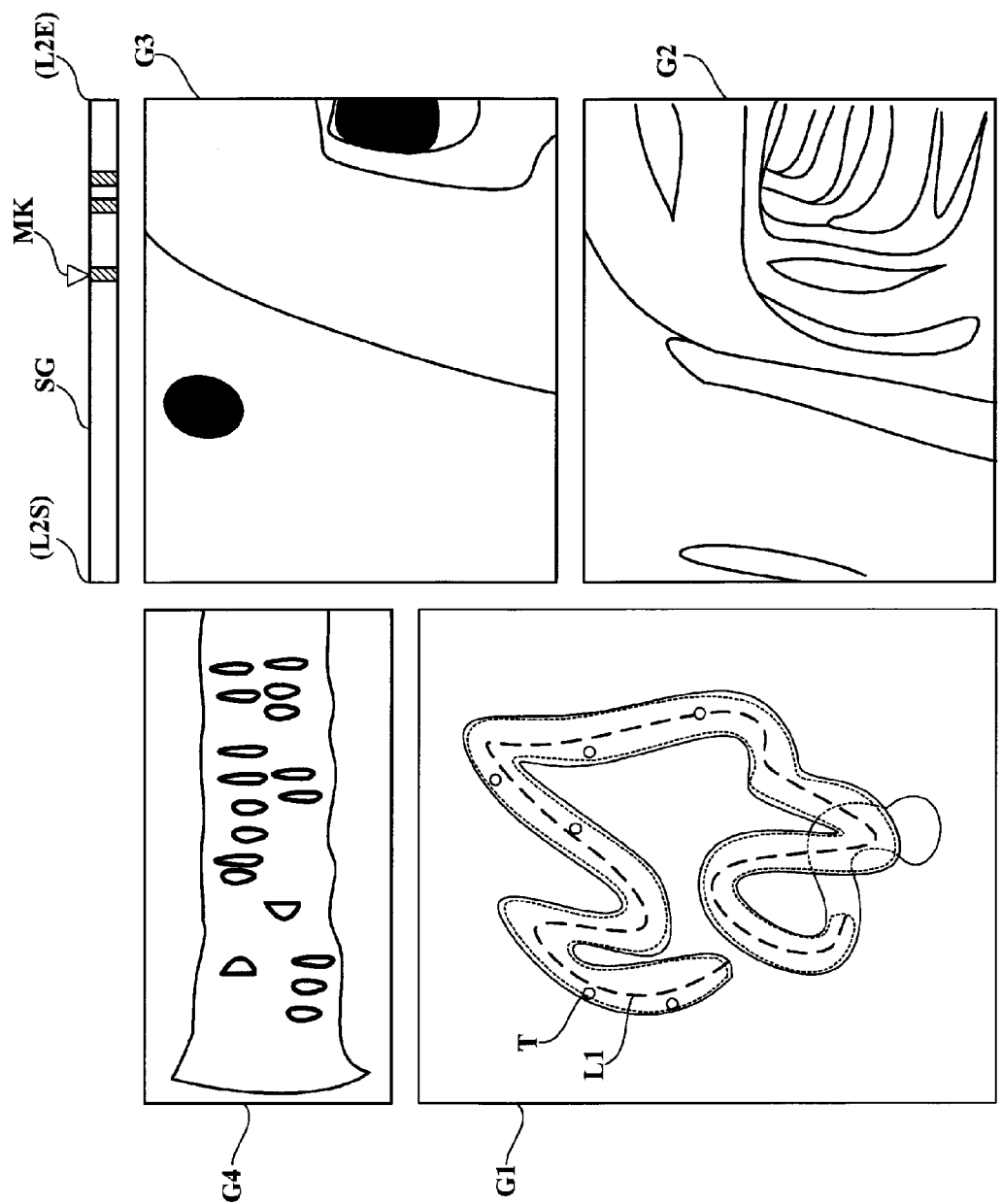
FIG. 7 is a diagram showing an example when a virtual endoscopic image and capsule endoscopic image are displayed in parallel.

Interlocking display is explained with references to FIG. 6 and FIG. 7. FIG. 6 is a figure in which a VR image, virtual endoscopic image, and capsule endoscopic image of the tubular body are displayed in parallel, while FIG. 7 is a figure in which a fillet view image is further arranged and displayed.

Moreover, FIG. 6 shows the location L1P of the viewpoint and the direction L1D of the line of sight in the virtual endoscopic image, as well as the location L2P of the virtual endoscope, and the direction L2PD of the line of sight of the capsule endoscope. Moreover, the VR image G1, the virtual endoscopic image G2, and the capsule endoscopic image G3 of the tubular body displayed in parallel are also shown. FIG. 7 shows the fillet view image G4 and other images G1 to G3 displayed in parallel.

As a specific method of interlocking display, displaying is carried out by vertically or horizontally displaying in parallel, and/or displaying by switching in response to an operation by the operator using the GUI 20, etc.

As shown in FIG. 6 and FIG. 7, the three-dimensional images stored in the three-dimensional image storage 11 are used to display the VR (volume Rendering) images of the CT in parallel, and the present line of sight as well as the viewpoint of the first central line, second central line, virtual endoscopic image, and capsule endoscopic image, and the lesion candidate location, etc., are graphically shown on the VR image (refer to FIG. 6). Thereby, the lesion candidate location, etc., becomes easier to comprehend due to the positional relation of the virtual endoscopic image and the capsule endoscopic image that are displayed.

For similar purposes, a fillet view image, which is the VR image that is obtained by cutting the tubular body open along the first central line, is displayed (Refer to FIG. 7). (S204)

In S204, it is determined whether or not displaying of the images is terminated. When determined that displaying of the images is terminated (S204: Yes), displaying of the images is terminated. When determined that displaying of the images is not terminated (S204: No), it switches over to S205, which determines whether or not the location on the first central line is changed.
(S205)

In S205, when the operator changes the viewpoint and line of sight of the virtual endoscopic image and/or the capsule endoscopic image by an operation of the GUI 20 (S205: Yes), the capsule endoscopic image selecting part 17 receives the change of the viewpoint and/or the line of sight, and re-selects the capsule endoscopic image (S202).

The display controller 22 displays, in an interlocking fashion, the capsule endoscopic image obtained in S202 and the virtual endoscopic image generated in S203 on the monitor 23 based on the location and/or the direction on the first central line that are/is changed.

As an example of the operation according to the GUI 20, the location of the viewpoint and the direction of the line of sight are changed by specifying the location and the direction wished to be observed upon the VR image of CT by the inputting part 21. By means of this operation, the operator specifies the lesion candidate location displayed on the VR image, thereby display of the virtual endoscopic image and the capsule endoscopic image are updated based on the present location of the viewpoint and the direction of the line of view on the VR image G1. Therefore, the capsule endoscopic image may be instantly observed according to the location of the viewpoint and the direction of the line of sight.

As another example of the operation according to the GUI 20, by, for example, means of moving the inputting part 21, such as a mouse, in the direction that the operator wishes to observe on the virtual endoscopic image or the capsule endoscopic image, the lines of sight of both images are changed in an interlocking fashion. By means of this operation, the lesion candidate may be three-dimensionally observed from various angles even regarding the capsule endoscopic image.

It should be noted that when the viewpoint and the line of sight are not changed (S205: No), it returns to S204, which determines whether or not displaying of the images is terminated.

Second Embodiment

Next, the medical image displaying apparatus related to the second embodiment is described with reference to FIGS. 10 to 12.

Figure 10:
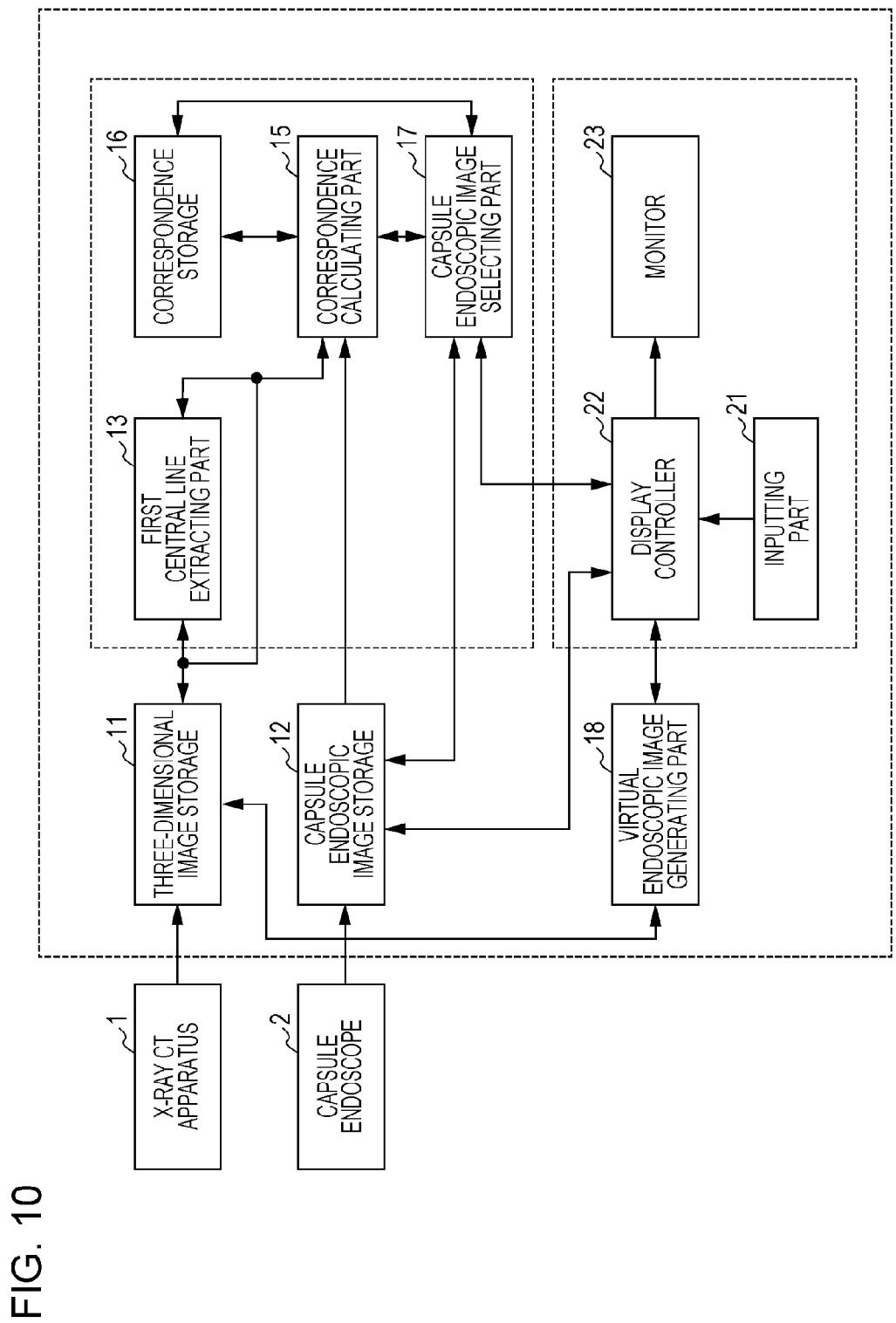
FIG. 10 is a block diagram showing the configuration of the medical image displaying apparatus related to the second embodiment.
Figure 11:
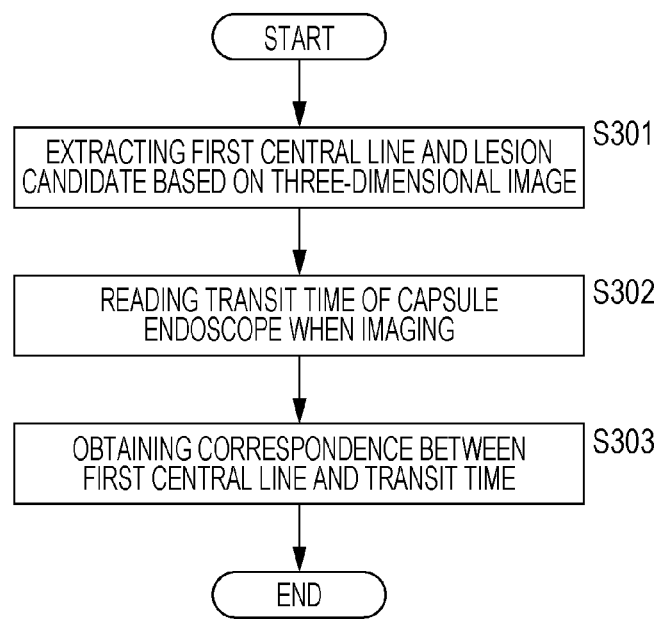
FIG. 11 is a flow chart showing the series of actions in obtaining a correspondence between the first central line and a transit time of the capsule endoscope.

FIG. 10 is a configuration block diagram of the medical image displaying apparatus.

As shown in FIG. 1 and FIG. 10, the difference with the first embodiment is that while the correspondence calculating part 15 related to the first embodiment obtains a correspondence between the first central line and the second central line from the correspondence of the first central line and the second central line, the correspondence calculating part 15 related to the second embodiment obtains a correspondence between the first central line and the transit time when the capsule endoscope passes inside the tube of the tubular body.

Hereafter, differing points are described and descriptions on the same configurations as the first embodiment are omitted.

The correspondence calculating part 15 obtains the correspondence between the location on the first central line and the transition time of the capsule endoscope based on the statistical average speed at which the capsule endoscope moves inside the tubular body.

Next, an example of obtaining the correspondence is explained.

The imaging starting time in imaging using the capsule endoscope is referred to as ts, the imaging termination time is referred to as te, the transit time is referred to as ta, and the average speed of the motion of the capsule endoscope is referred to as v. it should be noted that the transit time ta is stored in the capsule endoscopic image storage 12 accompanying the capsule endoscopic image at the imaging.

The time required for imaging To is obtained by subtracting the imaging starting time from the imaging termination time (te−ts). Moreover, the required time Ta until transit time ta is obtained by subtracting the imaging starting time from the transit time ta (ta−ts).

The approximate location of the capsule endoscope in the entire transition course at the transit time ta is obtained by comparing the time required for imaging To and Ta (Ta/To).

The total length Lo of the first central line may be obtained by integrating the small distances between points from the starting point L1S to the end point L1E. Moreover, the length La from the starting point L1S to the location L1P on the first central line is obtained by integrating the small distances between points from the starting point L1S to the location L1P on the first central line.

The approximate location L1P on the first central line in the total length of the first central line may be obtained by comparing the total length Lo of the first central line and the length La from the starting point to the location L1P on the first central line (La/Lo).

Both the locations obtained are correlated to each other [(Ta/To)≈(La/Lo)]. Thereby, the length La along the first central line from the starting point L1S is obtained from the transit time ta (or Ta), the time required for imaging To, and the total length Lo of the first central line, and the location L1P on the first central line is obtained.

Due to the correspondence calculating part 15 being configured in the above manner, the correspondence storage 16 and the capsule endoscopic image selecting part 17 are configured as follows.

The correspondence storage 16 stores the correspondence between the locations on the first central line and the transit times. Furthermore, the capsule endoscopic image selecting part 17 reads out the transit time corresponding to the location on the first central line from the correspondence storage 16 and selects the image taken at a time close to the transit time from among the capsule endoscopic images stored in the capsule endoscopic image storage 12.

Next, the series of actions in obtaining the correspondence between the first central line and the transit time of the capsule endoscope is described with reference to FIG. 11. FIG. 11 is a flow chart showing the series of actions in obtaining the correspondence between the first central line and the transit time of the capsule endoscope.

(S301)

In S301, the first central line and the lesion candidate are extracted based on three-dimensional images in the same manner as S101 in the first embodiment.

(S302)

In S302, the correspondence calculating part 15 reads the transit time of the capsule endoscope at the time of imaging from the capsule endoscopic image storage 12.

(S303)

Next, in S303, the correspondence calculating part 15 obtains the correspondence between the location and the transit time of the first central line. The correspondence is stored in the correspondence storage 16.

Next, a series of actions in carrying out definitive diagnosis in the capsule endoscopy is described using correspondence. FIG. 12 is a flow chart showing the series of actions in selecting the capsule endoscopic image in which the lesion candidate is displayed.

(S401)

Figure 12:
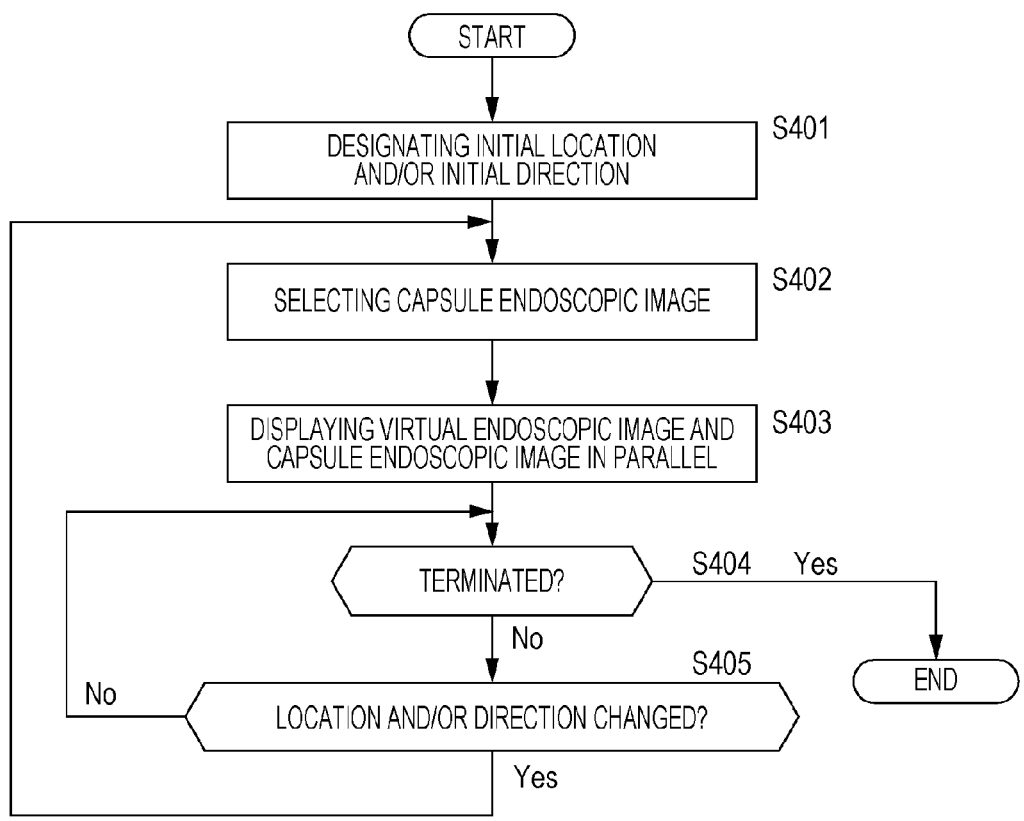
FIG. 12 is a flow chart showing a series of actions in selecting a capsule endoscopic image displaying the lesion candidate.

As shown in FIG. 12, in S401, the capsule endoscopic image selecting part 17 receives an instruction to start displaying the virtual endoscopic image and the capsule endoscopic image on the monitor 23, and reads the initial location and the initial direction on the first central line from the internal memory of the GUI 20.

(S402)

In S402, the capsule endoscopic image selecting part 17 obtains, based on the initial location on the first central line that has been read, the transit time of the capsule endoscope corresponding to the location on the first central line based on the table stored in the correspondence storage 16.

Next, the capsule endoscopic image selecting part 17 extracts the image group taken near the transit time from among the capsule endoscopic images stored in the capsule endoscopic image storage 12.

Next, the capsule endoscopic image selecting part 17 selects the image taken in the direction closest to the initial direction on the first central line stored in the GUI 20 in advance from among the image group. The selected image is determined as the capsule endoscopic image closest to the initial location and initial direction on the first central line.

(S403)

In S403, the virtual endoscopic image generating part 18 generates the virtual endoscopic image using the three-dimensional image stored in the three-dimensional image storage 11 based on the initial location and the initial direction on the first central line that are set in advance in the GUI 20.

The display controller 22 displays, in an interlocking fashion, the capsule endoscopic image obtained in S402 and the virtual endoscopic image generated in S403 on the monitor 23 based on the initial location and the initial direction on the first central line.

(S404)

In S404, it is determined whether or not displaying of the images is terminated. When displaying of the images is terminated (S404: Yes), displaying of the images is terminated. When displaying of the images is not terminated (S404: No), it switches over to S405, which determines whether or not the location on the first central line is changed.

(S405)

In S405, when the operator changes the viewpoint and the line of sight of the virtual endoscopic image and/or the capsule endoscopic image by an operation of the GUI 20 (S405: Yes), the capsule endoscopic image selecting part 17 receives the change of the viewpoint and/or the line of sight, and re-selects the capsule endoscopic image (S402).

The display controller 22 displays, in an interlocking fashion, the capsule endoscopic image obtained in S402 and the virtual endoscopic image generated in S403 on the monitor 23 based on the location and/or the direction on the first central line that are/is changed.

Modified Example 1

In the above, embodiments have been explained with CT large intestine analysis as an example.

Figure 13:
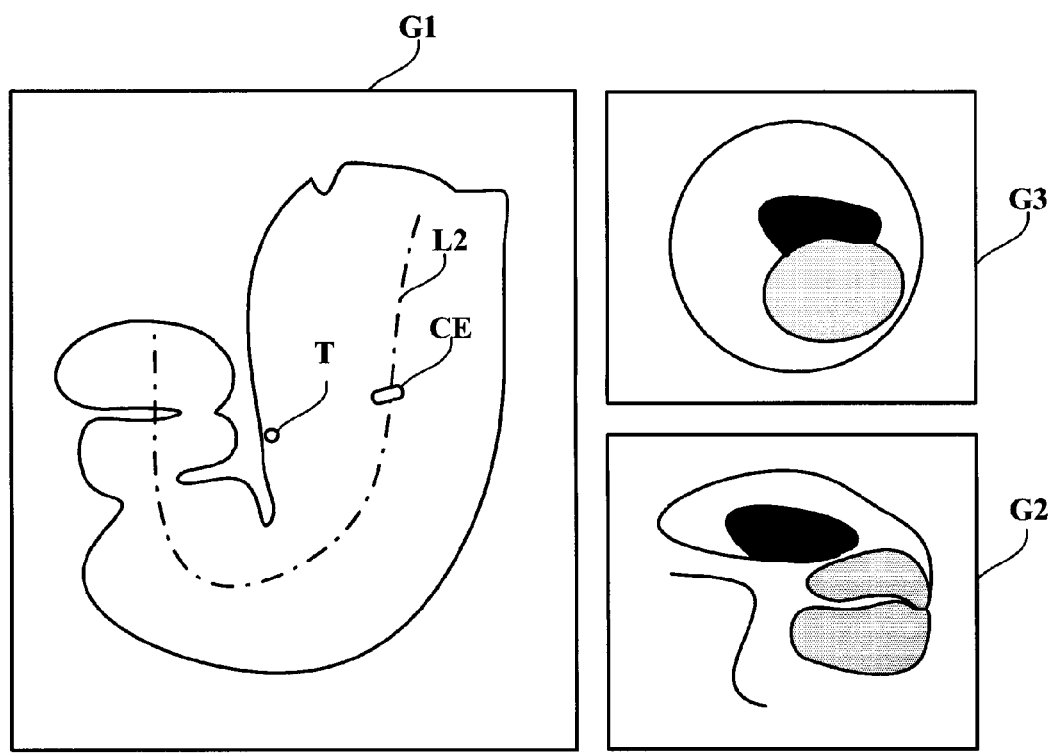
FIG. 13 is a diagram showing a display example with examination of the stomach as the subject.

Next, Modified Example 1 of the embodiment is described with reference to FIG. 13. FIG. 13 is a figure showing a displayed example with examination of the stomach as the subject. FIG. 13 shows the VR image G1 the virtual endoscopic image G2, and the capsule endoscopic image G3 of the tubular body displayed in parallel; furthermore, the lesion candidate T and the capsule endoscope CE are shown in the VR image G1.

As shown in FIG. 13, the present invention may be applied to the digestive tract in general such as for stomach analysis, etc., using similar methods.

In this embodiment, observation may be carried out focusing only on the capsule endoscopic image corresponding to the polyp lesion candidate location examined by a three-dimensional medical diagnosis apparatus such as the CT 1, etc.; therefore, the trouble of confirming all of a lot of images may be saved, improving the efficiency of examination when making a definitive diagnosis of the polyp lesion.

Moreover, in conjunction with fine adjustments of the direction of observing the polyp lesion candidate on virtual endoscopic images such as the CT 1, etc., the capsule endoscopic image of the corresponding direction is updated and displayed on all such occasions; thereby, the capsule endoscopic image may be observed as a virtual three-dimensional image, the lesion candidate may be diagnosed with a three-dimensional endoscopic image, and the diagnosis efficiency regarding the definitive diagnosis of polyp lesion is improved.

Modified Example 2

Next, Modified Example 2 of the embodiment is described with reference to FIG. 7.

In the embodiment mentioned above, when a virtual endoscopic image is selected, the capsule endoscopic image is displayed based on the location of the viewpoint of the virtual endoscopic image. In contrast, in Modified Example 2, when a capsule endoscopic image is selected, the location of the viewpoint corresponding to the transit time or the transit location of the capsule endoscope when the selected capsule endoscopic image is acquired is obtained, and the virtual endoscopic image is displayed based on the obtained location of the viewpoint.

FIG. 7 is a diagram showing an example when the virtual endoscopic image G2 and the capsule endoscopic image G3 are displayed in parallel. In FIG. 7, the scale image arranged along the edge of the capsule endoscopic image G3 is indicated as "SG."

As shown in FIG. 7, the left end position of the scale image SG is the transit starting time or transit starting location, and corresponds to the starting point L2S of the virtual endoscope shown in FIG. 6. The right end position of the scale image SG is the transit termination time or the transit termination location, and corresponds to the end point L2E of the virtual endoscope shown in FIG. 6.

Moreover, in FIG. 7, a representative color of the tissue corresponding to the transit time or the transit location of the capsule endoscope, which is a color on a plurality of capsule endoscopic images acquired by the capsule endoscope passing inside the tube, is displayed on the scale image SG. For example, the representative color of the lesion is expressed with "red" (hatching shown in FIG. 7).

A marker shown in a triangular shape is indicated as "MK" in FIG. 7. The capsule endoscopic image selecting part 17 comprises the inputting part 21 and the display controller 22. Due to an operation of the inputting part (for example, a mouse) 21, the location of the marker MK is displayed such that it may be moved along the scale image SG. The location of the marker MK corresponds to the transit time or the transit location of the capsule endoscope.

The display controller 22 receives a designation of the location of the marker MK by the operation of the inputting part 21, selects the capsule endoscopic image acquired at the transit time or the transit location corresponding to this location, and displays the selected capsule endoscopic image.

The correspondence calculating part 15 receives the selection of the capsule endoscopic image and obtains the location of the viewpoint (location on the first central line corresponding to the transit time or the transit location of the capsule endoscope when the selected capsule endoscopic images are acquired). The display controller 22 displays the virtual endoscopic image based on the obtained location of the viewpoint.

In the above embodiment, when the virtual endoscopic image and the capsule endoscopic image are associated and, for example, when the lesion candidate is designated on the virtual endoscopic images, it becomes easier to select the capsule endoscopic image on which the lesion candidate corresponding to this is displayed, improving the workability of definitive diagnosis in capsule endoscopy.

It should be noted that, in the embodiment, as shown in FIG. 6 and FIG. 7, the display controller 22 displaying the VR image G1, virtual endoscopic image G2, and capsule endoscopic image G3, etc. in parallel is described; however, the VR image G1, virtual endoscopic image G2, and capsule endoscopic image G3, etc., may be interchangeably displayed.

Furthermore, the display controller 22 may display by overlaying the location of the capsule endoscope with the virtual endoscopic image. The capsule endoscopic image selecting part 17 obtains the capsule endoscopic image closest to the location and direction on the first central part based on the location of the viewpoint (location on the first central line) and the direction of the line of sight (direction on the first central line) regarding the virtual endoscopic image. The display controller 22 displays by overlapping the location on the second central line in the obtained capsule endoscopic image (location of capsule endoscope) with the virtual endoscopic image. Thereby, the association between the virtual endoscopic image and the capsule endoscopic image becomes easier.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

EXPLANATION OF SYMBOLS

1 CT
2 Capsule endoscope
11 Three-dimensional image storage
12 Capsule endoscopic image storage
13 First central line extracting part
14 Second central line extracting part
15 Correspondence calculating part
16 Correspondence storage
17 Capsule endoscopic image selecting part
18 Virtual endoscopic image generating part
20 GUI
21 Inputting part
22 Display controller
23 Monitor

The invention claimed is:

1. A medical image displaying apparatus that, by using a previously captured three-dimensional image of the tubular body, is capable of displaying a virtual endoscopic image in a tube based on a viewpoint set inside the tube of the tubular body, comprising:
a capsule endoscopic image storage that stores capsule endoscopic images acquired by a capsule endoscope passing inside the tube;
a display controller that displays the capsule endoscopic images based on the location of the viewpoint;
a first central line extracting part that extracts a first central line of the tubular body based on the a previously captured three-dimensional image; and
a correspondence calculating part that obtains a correspondence between the first central line and the capsule endoscopic images, wherein
the display controller is configured to display the capsule endoscopic images based on the correspondence.

2. The medical image displaying apparatus according to claim 1, wherein,
the display controller displays the capsule endoscopic images based on the viewpoint specified upon the virtual endoscopic images.

3. The medical image displaying apparatus according to claim 1, wherein,
the display controller displays the location of the capsule endoscope by overlapping with the virtual endoscopic images.

4. The medical image displaying apparatus according to claim 1, further comprising:
a second central line extracting part that extracts a second central line of the tubular body based on the location of the capsule endoscope in advance, wherein
the correspondence calculating part obtains a correspondence between the first central line and the second central line.

5. The medical image displaying apparatus according to claim 4, wherein,
the correspondence calculating part obtains the correspondence based on the degree of similarity of the three-dimensional tangent vectors indicating the directions of the central lines in the first central line and the second central line.

6. The medical image displaying apparatus according to claim 4, wherein, the capsule endoscopic image storage stores the capsule endoscopic image by associating with the location of the second central line, which is the location of the capsule endoscope, and the direction of the second central line, which is the direction of the capsule endoscope, comprising a capsule endoscopic image selecting part that obtains the location on the second central line corresponding to the location on the first central line with reference to the correspondence, extracts an image group imaged in the periphery of the location on the obtained second central line from among the capsule endoscopic images stored in the capsule endoscopic image storage, obtains the direction of the second central line relatively closest to the direction of the first central line from the extracted image group, obtains the location on the second central line corresponding to the direction on the obtained second central line, and selects the capsule endoscopic image related to the location and the direction on the obtained second central line from among the capsule endoscopic images stored in the capsule endoscopic image storage.

7. The medical image displaying apparatus according to claim 1, the correspondence calculating part obtains a correspondence between the first central line and the transit time taken when the capsule endoscope passes inside the tube.

8. The medical image displaying apparatus according to claim 1, wherein, the display controller arranges and displays the virtual endoscopic image and the capsule endoscopic image in parallel.

9. The medical image displaying apparatus according to claim 1, wherein, the display controller displays the virtual endoscopic image and the capsule endoscopic image in an alternate fashion.

10. The medical image displaying apparatus according to claim 1, wherein, the virtual endoscopic image includes an opened image that is obtained by opening the inside of the tube along the central line of the tubular body.

11. A medical image displaying apparatus that, by using a three-dimensional image of the tubular body, is capable of displaying a virtual endoscopic image in a tube based on a viewpoint set inside the tube of the tubular body, comprising:

a capsule endoscopic image storage that stores multiple capsule endoscopic images acquired by a capsule endoscope passing inside the tube;

a means of, upon selection of the capsule endoscopic images, obtaining the location of the viewpoint corresponding to the transit time or the transit location of the capsule endoscope when the selected capsule endoscopic image has been acquired;

a display controller that displays a virtual endoscopic image based on the obtained location of the viewpoint;

a first central line extracting part that extracts a first central line of the tubular body based on the a previously captured three-dimensional image; and a correspondence calculating part that obtains a correspondence between the first central line and the capsule endoscopic images, wherein the display controller is configured to display the capsule endoscopic images based on the correspondence.

* * * * *